(12) United States Patent
Cummings et al.

(10) Patent No.: US 9,814,473 B2
(45) Date of Patent: Nov. 14, 2017

(54) GUIDANCE SYSTEM AND METHOD FOR BONE FUSION

(71) Applicant: Wright Medical Technology, Inc., Memphis, TN (US)

(72) Inventors: Shannon Cummings, Hernando, MS (US); Kian-Ming Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 240 days.

(21) Appl. No.: 14/421,049

(22) PCT Filed: Sep. 11, 2014

(86) PCT No.: PCT/US2014/055161
§ 371 (c)(1),
(2) Date: Feb. 11, 2015

(87) PCT Pub. No.: WO2016/039756
PCT Pub. Date: Mar. 17, 2016

(65) Prior Publication Data
US 2016/0256175 A1   Sep. 8, 2016

(51) Int. Cl.
| | |
|---|---|
| A61B 17/58 | (2006.01) |
| A61B 17/60 | (2006.01) |
| A61F 2/00 | (2006.01) |
| A61B 17/17 | (2006.01) |
| A61B 17/00 | (2006.01) |

(52) U.S. Cl.
CPC ...... *A61B 17/1703* (2013.01); *A61B 17/1717* (2013.01); *A61B 17/1796* (2013.01); *A61B 17/1775* (2016.11); *A61B 2017/0092* (2013.01)

(58) Field of Classification Search
None
See application file for complete search history.

(56) References Cited

U.S. PATENT DOCUMENTS

| | | | |
|---|---|---|---|
| 2,391,537 | A | 12/1945 | Anderson |
| 4,338,927 | A | 7/1982 | Volkov et al. |
| (Continued) | | | |

FOREIGN PATENT DOCUMENTS

| | | |
|---|---|---|
| CN | 103800049 A | 5/2014 |
| CN | 203790012 U | 8/2014 |
| (Continued) | | |

OTHER PUBLICATIONS

Patent Examination Report No. 1 Issued in connection with corresponding Australian patent application No. 2014324172, May 16, 2016, 8 pages.

(Continued)

*Primary Examiner* — Sameh Boles
(74) *Attorney, Agent, or Firm* — Duane Morris LLP (57) ABSTRACT

An apparatus comprises a medial rail having a plurality of openings through the medial rail for receiving pins, screws or wires. An arm is pivotally mounted to the medial rail. The arm has at least a first track on a first side. A post has a connector slidably mounted to the first track of the arm for movement along the first track. A guide is slidably mounted for movement along the post. The guide has at least one opening through it and at least one pin for engaging a bone of a patient.

6 Claims, 9 Drawing Sheets

(56) References Cited

U.S. PATENT DOCUMENTS

| | | |
|---|---|---|
| 6,755,838 B2 | 6/2004 | Trnka |
| 7,291,148 B2 | 11/2007 | Agee |
| 8,636,744 B2 | 1/2014 | Tochigi et al. |
| 9,592,064 B2 | 3/2017 | Biedermann et al. |
| 2003/0225406 A1 | 12/2003 | Weiner et al. |
| 2009/0270864 A1* | 10/2009 | Poncet ............... A61B 17/1684 |
| | | 606/83 |
| 2009/0275944 A1 | 11/2009 | Huebner et al. |
| 2010/0256687 A1 | 10/2010 | Neufeld et al. |
| 2013/0090662 A1 | 4/2013 | Hanson et al. |

FOREIGN PATENT DOCUMENTS

| | | |
|---|---|---|
| EP | 1247493 A1 | 10/2002 |
| SU | 1184530 A | 10/1985 |
| WO | 2004/045451 A2 | 6/2004 |
| WO | 2013/025825 A2 | 2/2013 |

OTHER PUBLICATIONS

International Search Report and Written Opinion of the International Searching Authority issued for International patent application No. PCT/US2014/055161, May 21, 2015, 11 pages.

Office Action issued for corresponding Chinese patent application No. 201480037788.1, dated May 27, 2017, 6 pages.

Office Action issued for corresponding Japanese patent application No. 2016-536209, dated Jun. 6, 2017, 5 pages.

* cited by examiner

GUIDANCE SYSTEM AND METHOD FOR BONE FUSION

CROSS-REFERENCE TO RELATED APPLICATIONS

This application is a national phase entry under 35 U.S.C. §371 of international patent application No. PCT/US2014/055161, filed Sep. 11, 2014, the entirety of which is herein incorporated by reference.

FIELD

This application pertains generally to medical devices, and more particularly to a system and method for use in arthrodesis procedures, such as fusing damaged, deteriorating, or fractured navicular, cuboid and/or metatarsal bones.

BACKGROUND

Arthrodesis is a surgical procedure for artificially inducing joint ossification between two bones. Arthrodesis may be performed to relieve pain in a joint which cannot be managed by more conservative approaches, such as medication, splints, or the like. The typical causes of such pain are fractures which disrupt the joint, and arthritis. Arthrodesis may be performed for fusing damaged, deteriorating, or fractured talus, navicular, cuboid and metatarsal bones foot. Arthrodesis may be used to treat Charcot midfoot deformity, including bone resection and/or osteotomy to reduce deformity.

One solution has been to drive a K-wire in through the affected metatarsal, cuboid, navicular, and possibly the talus bone, crossing multiple joints.

Bone fractures of the mid-foot are difficult to fixate because of the geometry of the bones. For patients with poor quality, soft bone (e.g. Charcot), this problem is exacerbated. It is difficult to maintain the proper alignment of these bones for performing fixation. It is difficult to accurately drill the holes, and manually drilled holes extending from the metatarsal to the talus were not always straight.

Improved methods for mid-foot and distal foot surgery are desired.

SUMMARY

In some embodiments, an apparatus comprises a medial rail having a plurality of openings therethrough for receiving pins, screws or wires. An arm is pivotally mounted to the medial rail. The arm has at least a first track on a first side thereof. A post has a connector slidably mounted to the first track of the arm for movement along the track. A guide is slidably mounted for movement along the post. The guide has at least one opening therethrough and at least one pin for engaging a bone of a patient.

In some embodiments, a method comprises: fixing a medial rail having a plurality of openings therethrough to a medial column of a patient for receiving pins, screws or wires; pivoting an arm pivotally mounted to the medial rail so the arm extends on a lateral side of the medial rail, the arm having at least a first track on a first side thereof, so that after the pivoting, the first track faces an anterior side of the arm; sliding a post having a connector slidably mounted to the first track of the arm for movement along the track until the post is adjacent a metatarsal to be treated; and sliding a guide slidably mounted for movement along the post, wherein the guide has at least one opening therethrough and one pin, and the sliding is performed for engaging until the pin engages a bone of a patient the metatarsal to be treated.

BRIEF DESCRIPTION OF THE DRAWINGS

These and other features and advantages of the present disclosure are more fully disclosed in, or rendered obvious by, the following detailed description, which is to be considered together with the accompanying drawings wherein like numbers refer to like parts and further wherein.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 11:
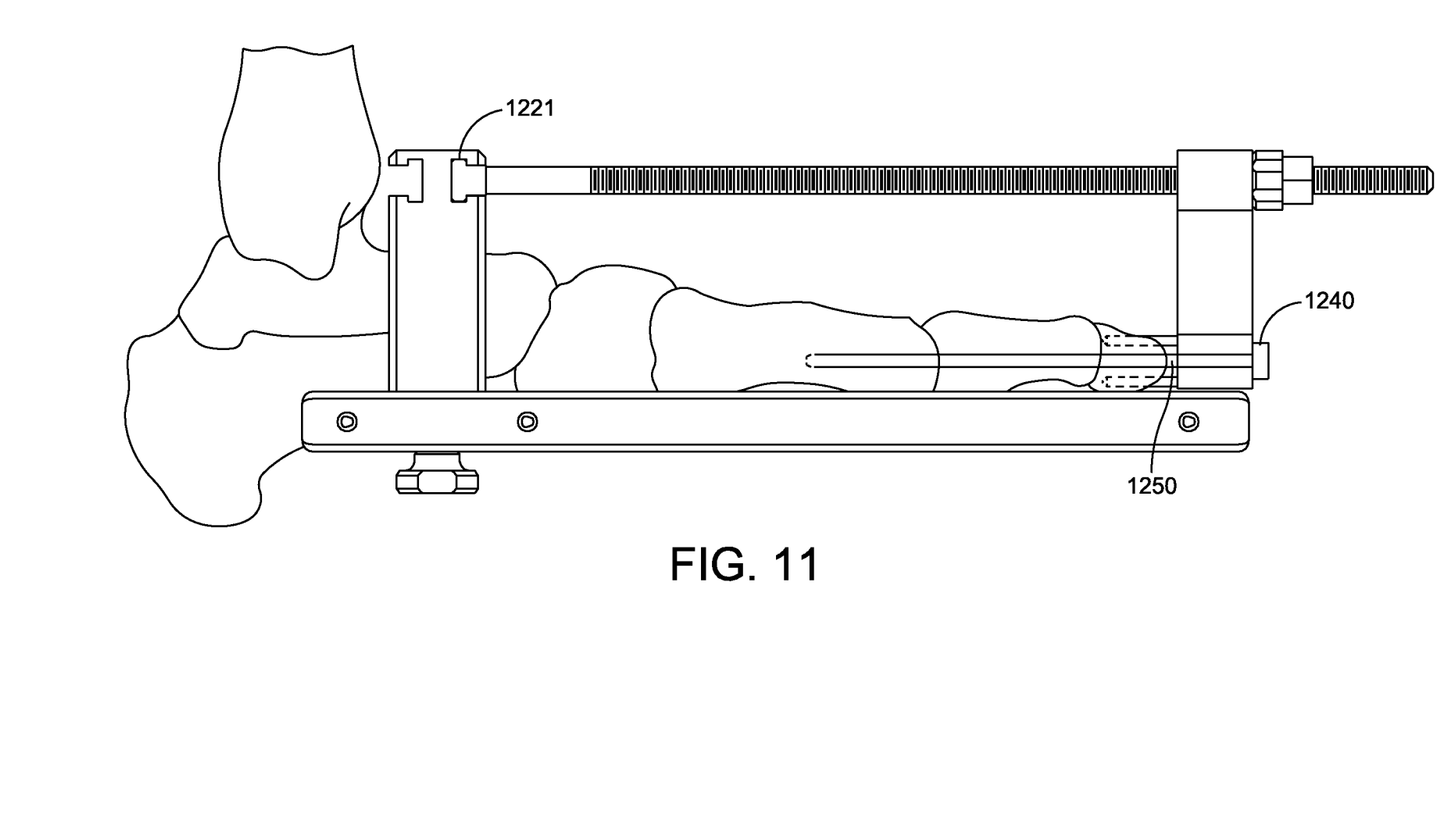
FIG. 11 is a medial view of the apparatus positioned on a foot of a patient.

A guidance system 1200 is described herein to facilitate the process of directing a wire 1250, bolt or beam (FIG. 11) from the distal end of the metatarsal to the mid or hind foot. The guidance system 1200 allows for drilling and/or implantation of a bolt/beam through the apparatus.

Figure 1:
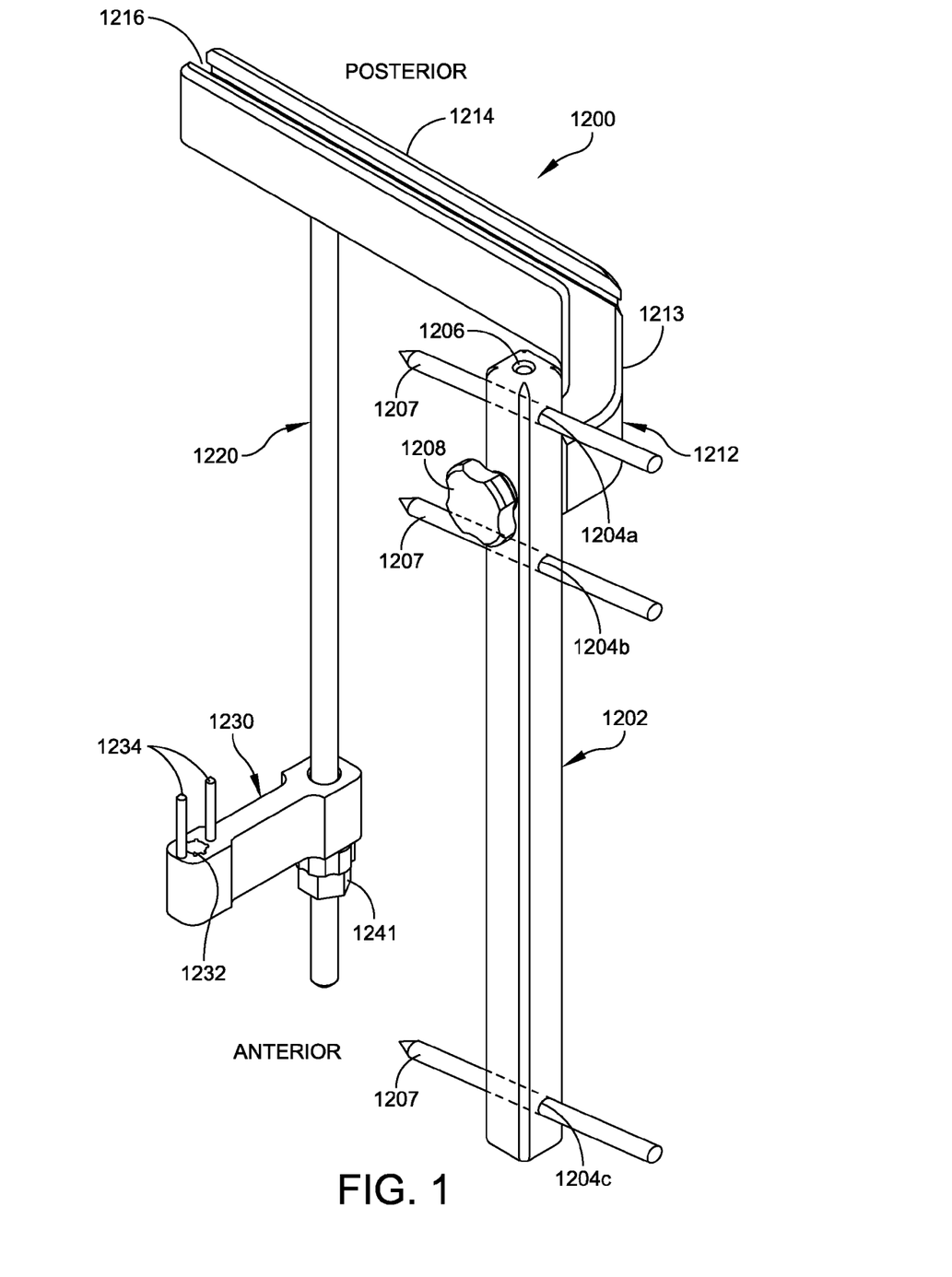
FIG. 1 is an isometric view of a guidance system according to an exemplary embodiment, as seen from a medial-plantar viewpoint.
Figure 2:
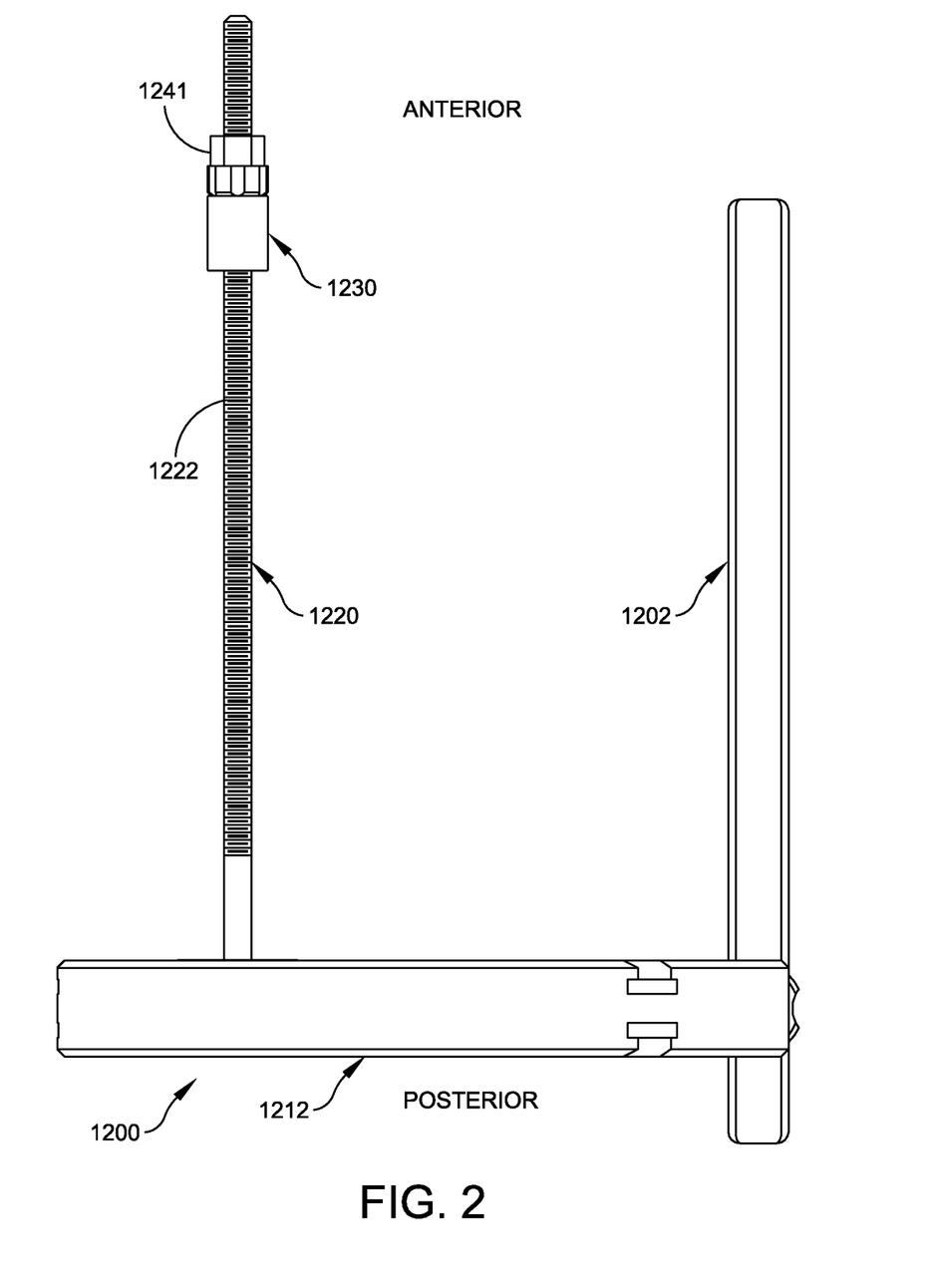
FIG. 2 is a dorsal plan view of the apparatus of FIG. 1.
Figure 5:
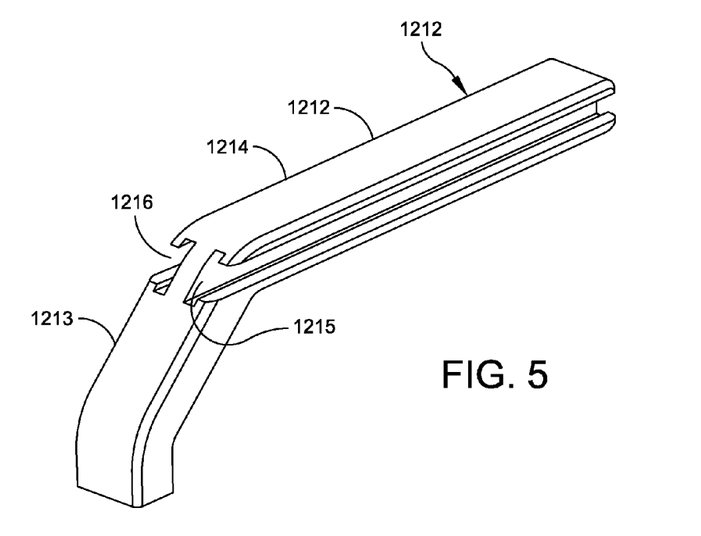
FIG. 5 is an isometric view of the arm of FIG. 1, as seen from a posterior-medial viewpoint.
Figure 6:
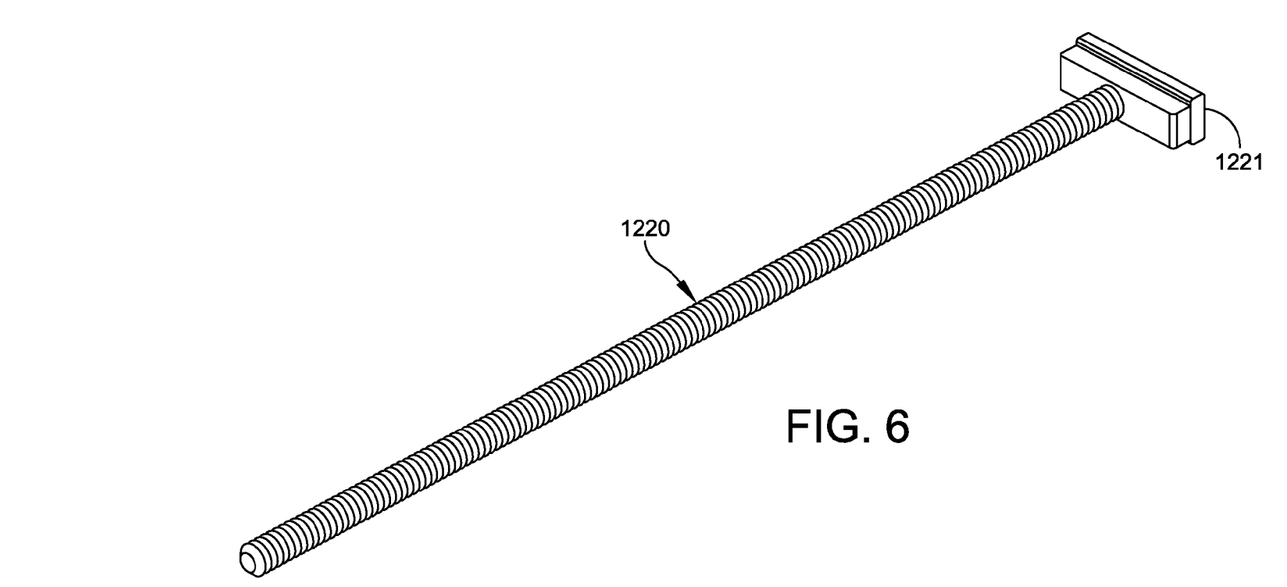
FIG. 6 is an isometric view of the post of FIG. 1, as seen from an anterior-dorsal viewpoint.
Figure 7:
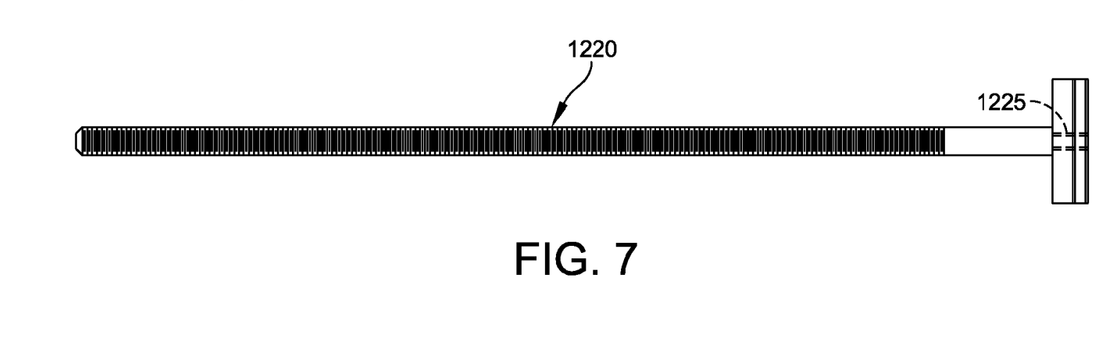
FIG. 7 is a dorsal plan view of the post of FIG. 6.
Figure 8:
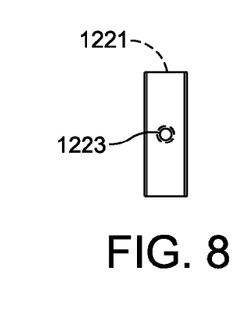
FIG. 8 is a lateral elevation view of the post of FIG. 6.
Figure 9:
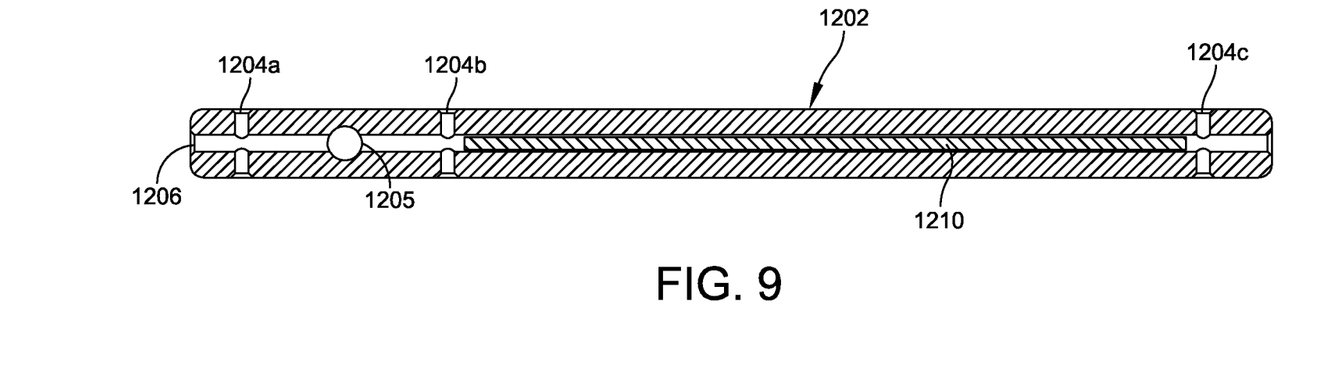
FIG. 9 is a cross-sectional view of the medial rail of FIG. 3, taken along section line 9-9 of FIG. 3.
Figure 10:
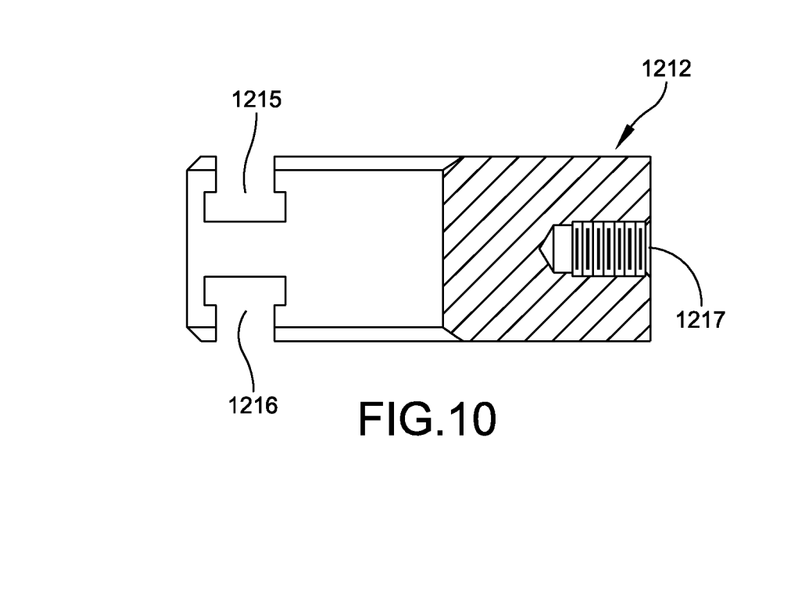
FIG. 10 is a cross-sectional view of the arm of FIG. 4, taken along section line 10-10 of FIG. 4.

FIGS. 1-10 show an exemplary embodiment of a guidance system. FIGS. 1-4 are isometric, dorsal, medial, and posterior views, respectively, of the apparatus 1200. FIG. 1 shows the apparatus as it would appear to a user at a plantar vantage point below the talus. FIGS. 5 and 10 show the arm 1212 of FIG. 1. FIGS. 6-8 show the post 1220 of FIG. 1. FIG. 9 shows the medial rail 1202.

The guidance system 1200 comprises a medial rail 1202 having a plurality of openings 1204a-1204c therethrough for receiving temporary fixation pins 1207, bolts (not shown), beams (not shown), or wires 1250 which fix the guidance system 1200 in proper alignment with the patient's foot. An arm 1212 is pivotally mounted to the medial rail 1202. The arm 1212 has at least a first track 1215 on a first side thereof. A post 1220 having a connector 1221 is slidably mounted to the first track 1215 of the arm 1212 for movement along the first track 1215. A guide 1230 is slidably mounted for movement along the post 1220. The guide 1230 has at least one opening 1232 therethrough and at least one pin 1234 for engaging a bone (e.g., a metatarsal) of a patient.

In some embodiments, the medial rail 1202 comprises a radiolucent material, and contains a radiopaque element 1210 (best seen in FIG. 9). For example, in some embodiments, the medial rail 1202 is made of polyetheretherketone (PEEK), another plastic, aluminum, or a carbon fiber reinforced composite material. In some embodiments, the radiopaque element 1210 is an elongated metal pin having a diameter that is smaller than a distance between the second side of the medial rail 1202 and a third side of the medial rail 1202 opposite the first side. The radiopaque element 1210 can be inserted in an axial passage 1206 along or parallel to a longitudinal axis of the medial rail 1202, where the longitudinal axis passes through the centroid of the medial rail. In some embodiments, the radiopaque element 1210 is positioned between two of the plurality of holes 1204b, 1204c of the medial rail 1202.

The medial rail 1202 has a bore 1205 extending therethrough. The bore 1205 extends in a dorsal-plantar (transverse) direction and passes through the central axis of the medial rail 1202. The bore 1205 receives a threaded member 1209 of the knob 1208, for locking the arm 1212 to the medial rail 1202. The arm 1212 can be pivoted by loosening the knob 1208 (and its threaded member 1209), and the arm 1212 can be locked in any angular position by tightening the knob 1208. The radiopaque element 1210 is positioned in the longitudinal direction so that it does not extend into the bore 1205 or interfere with the threaded member 1209.

In other embodiments, the central passage 1206 can extend partially through the medial rail 1202. For example, with the radiopaque element 1210 positioned between the openings 1204b and 1204c, the passage 1206 can extend between the opening 1204b and the end of passage 1206 opposite opening 1204b, or the passage 1206 can extend from the opening 1204c to the end of passage 1206 opposite opening 1204c, In other embodiments (not shown), the radiopaque element 1210 can be positioned along the length of the passage 1206 at other locations from that shown in FIG. 9. In some embodiments, the radiopaque element 1210 extends nearly all the way from opening 1204b to opening 1204c, and the passage 1206 and bore 1205 are arranged so that the radiopaque element 1210 does not intersect the threaded member 1209. For example, the radiopaque element 1210 can be shorter than that shown in FIG. 9, and can be positioned anywhere along the passage 1206 between opening 1204b and 1204c. Although FIG. 9 shows a single radiopaque element 1210, in other embodiments, two or more short radiopaque elements can be inserted in the passage 1206, between the openings 1204b and 1204c.

FIGS. 1-5 and 10 show the arm 1212. The arm 1212 has a medial-lateral portion 1214 with tracks 1215 and 1216 for deploying the post 1220 and guide 1230 to the appropriate position for a surgical procedure. The arm 1212 has a dorsal offset portion 1213, which elevates the medial-lateral portion 1214 of the arm 1212 above the dorsal surface of the foot. The arm 1212 has a first track 1215 on a first side thereof. In some embodiments, the arm 1212 has a second track 1216 on a second side of the arm 1212 opposite the first side of the arm 1212, and the post 1220 is capable of being slidably mounted to either the first track 1215 or the second track 1216. In some embodiments, the first track 1215 and second track 1216 are T-shaped. In other embodiments (not shown) the first track and second track are dovetail-shaped.

In some embodiments having two tracks 1215 and 1216, the arm 1212 is capable of pivoting about 180 degrees or more. The ability to pivot 180 degrees or more makes the guidance system 1200 a universal device, enabling use of a single guidance system 1200 for either the left or right foot. FIGS. 1-4 show the arm 1212 positioned for use on the patent's left foot. The medial rail 1202 is positioned to be affixed to the medial column of the left foot, and the arm 1212 extends from the medial rail 1202 in the lateral direction. To use the same guidance system for treating the right foot, the knob 1208 is loosened, the arm 1212 is pivoted by 180 degrees, and the knob is tightened. This position is shown in phantom in FIG. 4.

The post 1220 is configured to be alternatively mounted to the second track 1216 and arranged approximately parallel to the medial rail 1202 on a second side of the medial rail 1202 opposite the first side of the medial rail 1202. The post 1220 is removed from the first track 1215 and inserted in the second track 1216, which will now be facing in the posterior direction, toward the talus.

FIGS. 1-3 and 6-8 show an example of a post 1220 according to some embodiments. The medial rail 1202 is pinned to the bones of the medial column. The arm 1212 is perpendicular to the medial rail 1202, and the post 1220 is perpendicular to the arm 1212. Thus, the post 1220 is configured to be mounted to the first track 1215 and arranged parallel to the medial rail 1202 on a first side of the medial rail 1202. Because the medial rail 1202 of the guidance system 1200 is aligned with the medial column, then the post 1220 will be parallel to the first metatarsal for correct fixation of the bones to be treated. For brevity, the post 1220 is generally referred to herein as extending longitudinally in the anterior-posterior direction, but the orientation of the arm 1212 is perpendicular to the metatarsal, and the post 1220 is parallel to the metatarsal.

In some embodiments, the first track 1215 is a T-shaped groove (best seen in FIG. 10) or dovetail-shaped groove (not shown), and the connector 1221 is a T-shaped member (best seen in FIGS. 6-8) or dovetail-shaped member (not shown), where the shape of the connector 1221 corresponds to the shape of the first track. This allows the post 1220 to slide along the first track 1215 in the medial-lateral direction. In some embodiments, the first track 1215 and second track 1216 extend throughout the length of the medial-lateral portion 1214 of arm 1212, and are open at both ends. This permits the connector 1221 of post 1220 to be inserted in and removed from either end of either track 1215, 1216. In other embodiments, the first track 1215 and/or second track 1216 is (are) open only at one end (e.g., the anterior end).

In some embodiments, the post 1220 has a threaded end 1223 (shown in FIG. 7), and the connector 1221 has a threaded hole 1225 therethrough for receiving the threaded end 1223 of the post 1220. In some embodiments, the threaded end 1223 extends completely through the passage 1225, such that when the threaded end 1223 of the post 1220 is advanced to abut a back surface of the first track 1215, the post 1220 is locked in position with respect to the first track 1215. A small bearing force by the flat surface of the threaded end 1223 against the back surface of the first track 1215 is sufficient to prevent any medial-lateral movement within the track.

Generally, the post 1220 is not subjected to medial-lateral forces during the fusion procedure. Thus, in alternative embodiments, the post 1220 and connector 1221 can be formed as a single, unitary member, without any locking mechanism for preventing medial-lateral movement of the post 1220 within the track. When the surgeon presses the pins 1234 of the guide 1230 into the metatarsal, the guide 1230 maintains the post 1220 in the desired medial-lateral position with the first track 1215, for the duration of the procedure.

In other embodiments (not shown), the tracks 1215, 1216 can have a shape different from the T-shape shown, and the connector 1221 of the post 1220 has a different shape that corresponds to the shape of the track.

Figure 3:
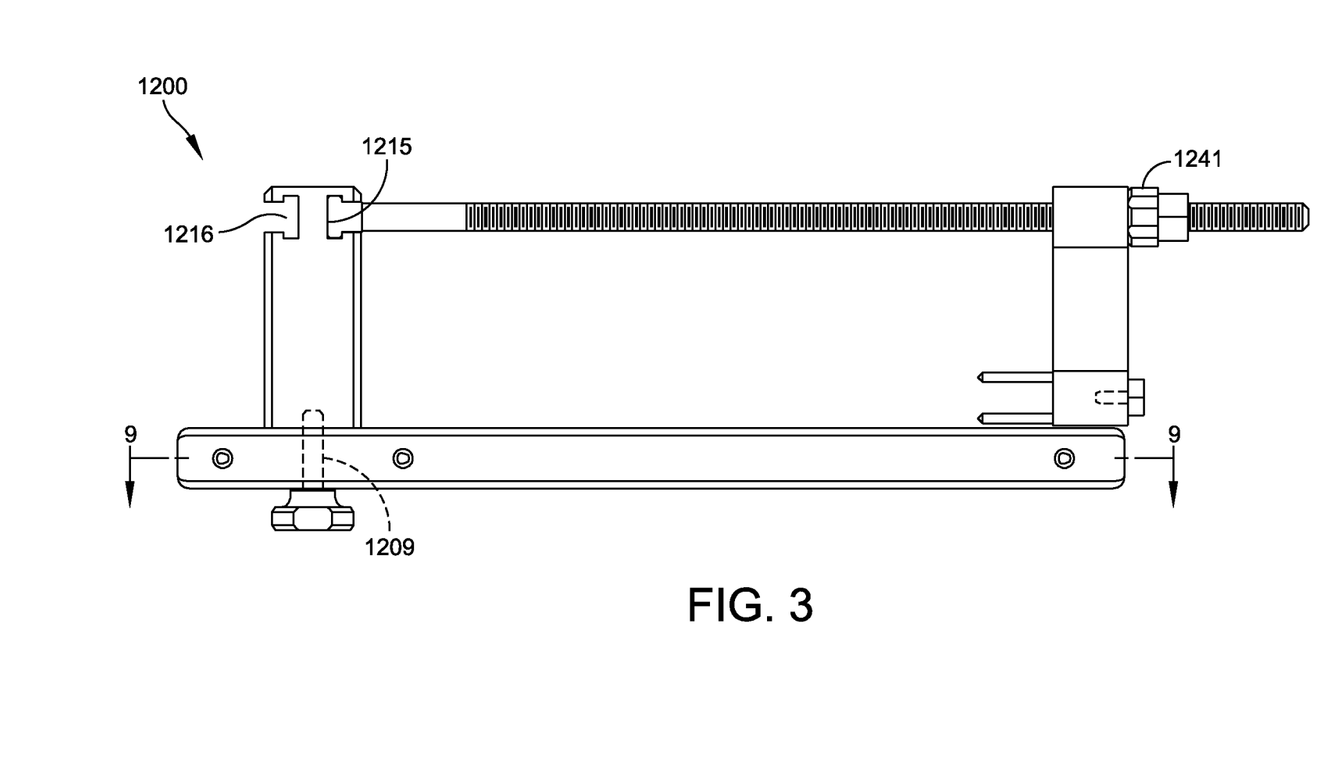
FIG. 3 is a medial side elevation view of the apparatus of FIG. 1.
Figure 4:
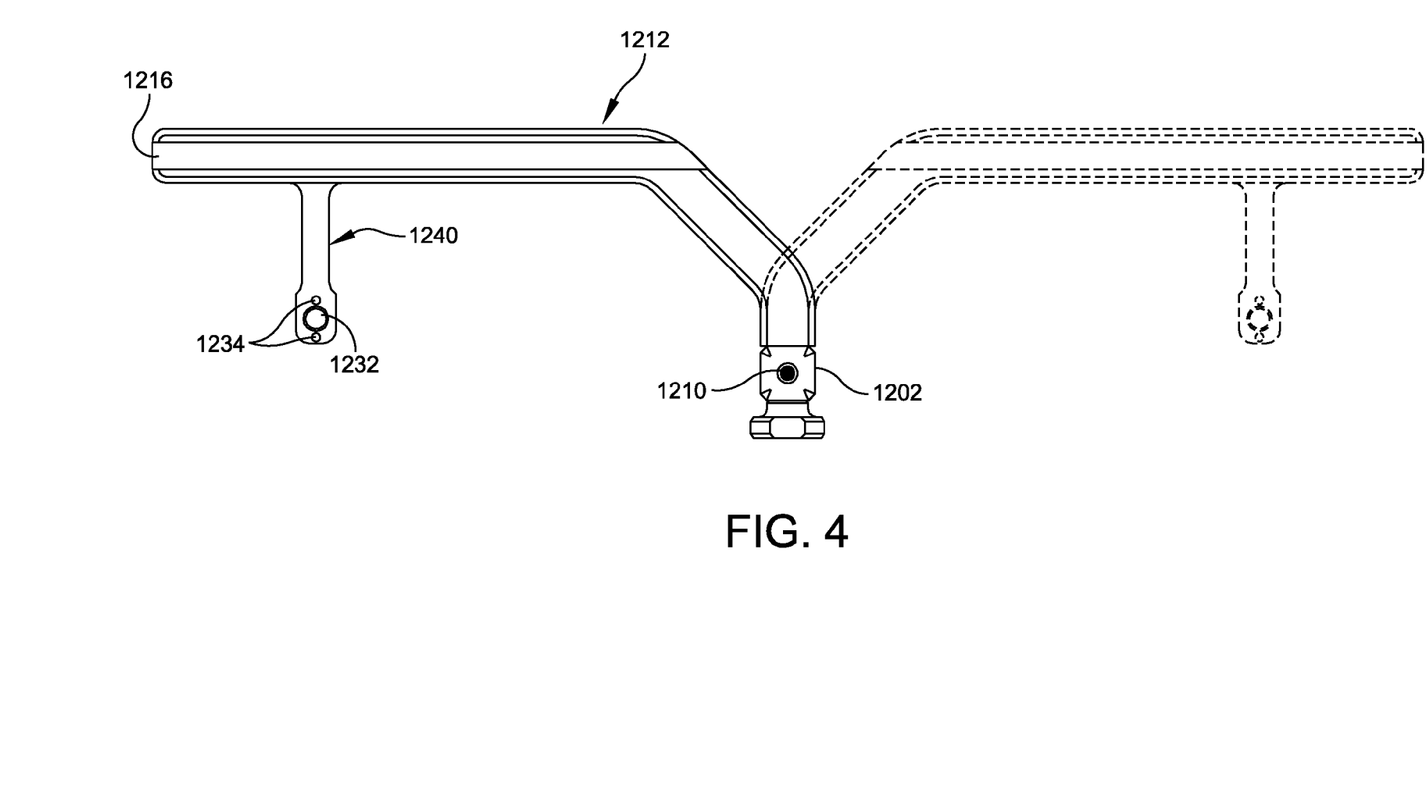
FIG. 4 is a posterior elevation view of the apparatus of FIG. 1.

The guide 1230 compresses the joints. Guide 1230 serves as a targeting guide for a wire 1250, beam or bolt, providing alignment and compression of joints, and acting as an alignment guide to prepare a hole and then to insert a wire 1250, beam or bolt into the medial column (or other bones to be treated). The guide is slidably mounted on the post 1220 for anterior-posterior movement. The guide 1230 has an opening 1232 for receiving a bushing 1240 (FIG. 3). The bushing 1240 can be configured with an appropriate interior opening size for any given wire 1250, beam, bolt or drill to be used, so that a single guide 1230 can accommodate a variety of wires 1250, beams (not shown) and bolts (not shown), by inserting a different bushing 1240 in the opening 1232 of the guide 1230. In some embodiments, the guide 1230 is configured with a handle (not shown) for ease of gripping and manipulation by the user.

Figure 12:
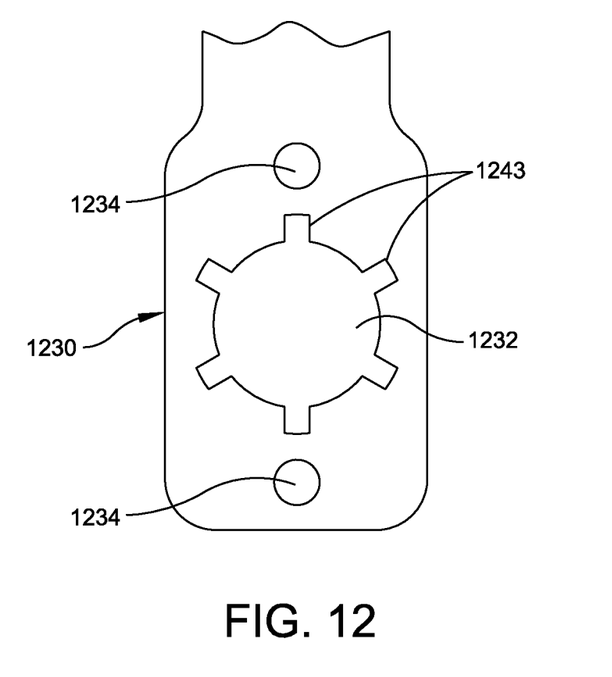
FIG. 12 is an enlarged view of the guide of FIG. 1.
Figure 13:
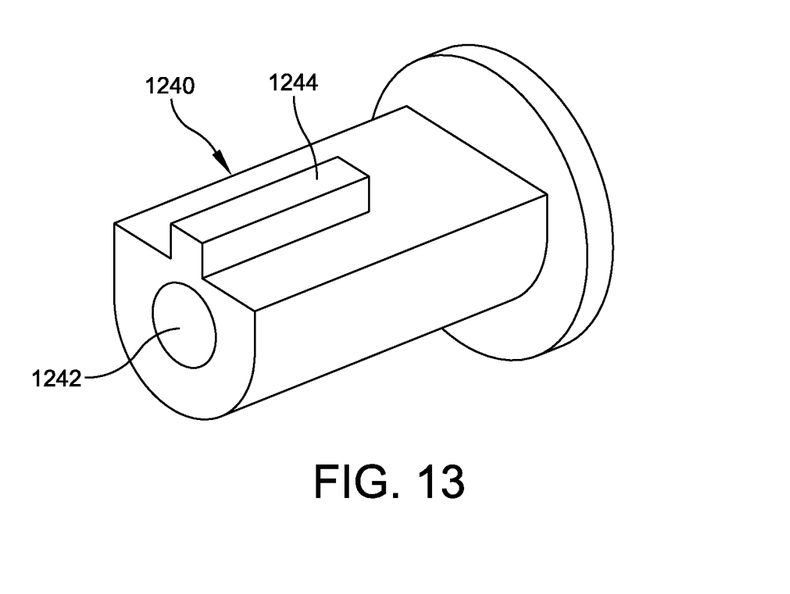
FIG. 13 is an isometric view of the bushing shown in FIG. 11.

The apparatus further comprises a bushing 1240 (FIG. 13) configured to be detachably mounted in the opening 1232 (FIG. 12) of the guide 1230. The bushing 1240 has a longitudinal passage 1242 adapted to receive a drill or a wire 1250 therethrough. For example, the surgeon can insert a K-wire 1250 through the passage 1242 of the bushing 1240 and then insert the drill through the passage 1242 of the bushing 1240 to drill over the K-wire 1250 through successive bones, including the metatarsal, cuboid, navicular, and possibly talus. The bushing 1240 can be provided with various sizes for longitudinal passage 1242. For example a first bushing 1240 can have a passage 1242 adapted to receive a K-wire 1250. A second bushing 1240 can have a passage 1242 adapted to receive a pin (not shown). A third bushing 1240 can have a passage 1242 adapted to receive a drill or driver (not shown). The first, second and third bushings can all have the same outer shape and size, with only the passage 1242 varied In some embodiments, the opening 1232 of the guide 1230 has a plurality of slots 1243 (FIG. 12) and the bushing has a corresponding key 1244 (FIG. 13) adapted to fit in one of the slots 1243. The slot and key arrangement prevents the bushing 1240 from rotating within the opening 1232.

In some embodiments, a method of using the guidance system comprises fixing the medial rail 1202 having a plurality of openings 1204*a*-1204*c* therethrough to a medial column of a patient by inserting pins 1207, wires, bolts, beams through the openings 1204*a*-1204*c* into the bone. In some embodiments, the medial rail 1202 comprises a radiolucent material, and contains a radiopaque element 1210. The surgeon views the radiopaque element 1210 with a fluoroscope to align the medial rail 1202 parallel to the metatarsal to be treated.

Temporary fixation pins (not shown) are driven through the openings 1204*a*-1204*c* at the desired location to fix the medial rail 1202 to the foot.

The knob 1208 is loosened, and the arm 1212 mounted to the medial rail 1202 is pivoted, so the arm 1212 extends on a lateral side of the medial rail 1202. After the pivoting, the medial-lateral portion 1214 is located laterally with respect to the medial rail 1202, and the first track 1215 (for a left foot procedure) or the second track 1216 (for a right foot procedure) faces the talus, i.e., faces an anterior side of the arm 1212.

With the arm 1212 in the desired position, the knob 1208 is tightened to secure the arm 1212.

The surgeon slides the post 1220 along the first track 1215 of the arm 1212 until the post 1220 is adjacent a metatarsal to be treated. In some embodiments, the user can lock the post 1220 into position by advancing the threaded end 1223 of the post 1220 towards the rear surface of the track 1215 (1216).

The surgeon makes an incision to expose the head of the metatarsal to be treated.

The surgeon slides the guide 1230 along the post 1220, until the pin 1234 engages the metatarsal to be treated. The surgeon presses the pins 1234 of the guide into the metatarsal, which fixes the medial-lateral position of the post 1220 if the post does not have a medial-lateral locking mechanism. The surgeon can use the nut 1241 to drive the pins 1234 of guide 1230 into the bone, and hold the guide 1230 in place on the post 1220. Alternatively, the surgeon can press the guide 1230 into place, and then advance the nut 1241 till it reaches the guide 1230.

Following positioning of the guide 1230, the user inserts a bushing 1240 into the guide, suitable for receiving a wire 1250, fusion bolt, fusion beam or driver. A fusion bolt (not shown) is a solid-core cylindrical implant of about 70 mm to about 180 mm length. A fusion beam (not shown) is a cylindrical implant of about 80 mm to about 180 mm length having a cannulated design to facilitate placing the implant over a K-Wire 1250. Following insertion of the bushing 1240, the surgeon drills an opening through the bushing 1240, and the wire 1250, fusion bolt or fusion beam is inserted into the metatarsal through the guide 1230.

In some embodiments, the surgeon inserts a first bushing 1240 in the guide 1230 and inserts a K wire 1250 into the bones. With the K wire 1250 in place, the surgeon removes the first bushing 1240 and inserts a larger bushing (not shown) into the opening 1232 of the guide. The bushing allows the surgeon to drill over the wire 1250 without changing the position of the guide 1230 or post 1220, so that the drilled hole is aligned with the location of the original wire 1250. In some embodiments, the inserting step includes passing the wire 1250 or drill through bone until the wire 1250 or drill reaches a talus of the patient.

If the patient's other foot will also be treated, the same guidance system 1200 can be used. If the guidance system 1200 is currently arranged for use on the left foot, and is to be used to treat the right foot, the arm 1212 is pivoted by approximately 180 degrees, so that a second track 1216 on a second side of the arm 1212 opposite the first side of the arm 1212 faces the anterior side of the arm 1212, and the post 1220 is mounted to the second track 1216. The user slides the post 1220 along the second track 1216 of the arm 1212 until the post 1220 is adjacent a second metatarsal to be treated, and slides the guide 1230 along the post 1220 until the pin 1234 engages the second metatarsal to be treated.

In addition to providing compression and aligning the drill for accurate hole preparation, the guidance system described herein frees up one of the surgeon's hands. The surgeon does not need to hold the metatarsal, cuboid, navicular and/or talus throughout the drilling. The surgeon can make a straight accurate hole from the metatarsal to the talus. The surgeon can insert a K wire 1250 and drill over the K wire 1250 without repositioning the guide 1230 of the guidance system, to ensure accurate alignment and drilling.

Although the subject matter has been described in terms of exemplary embodiments, it is not limited thereto. Rather, the appended claims should be construed broadly, to include other variants and embodiments, which may be made by those skilled in the art.

What is claimed is:

1. Apparatus comprising: a medial rail having a plurality of openings therethrough for receiving pins, screws or wires; an arm pivotally mounted to the medial rail, the arm having at least a first track on a first side thereof; a post having a connector slidably mounted to the first track of the arm for movement along the first track; and a guide slidably mounted for movement along the post, the guide having at least one opening therethrough and at least one pin for engaging a bone of a patient, wherein the arm has a second track on a second side of the arm opposite the first side of the arm, wherein the arm is capable of pivoting about 180 degrees or more, the post is configured to be slidably mounted to the first track and arranged approximately parallel to the medial rail on a first side of the medial rail, and the post is configured to be slidably mounted to a second track and arranged approximately parallel to the medial rail on a second side of the medial rail opposite the first side of the medial rail, wherein the connector has a threaded hole therethrough for receiving a threaded end of the post, such that advancing the threaded end of the post to abut a surface of the first track locks the post in position with respect to the first track.

2. The apparatus of claim 1, wherein the first track is a T-shaped or dovetail-shaped groove, and the connector is a T-shaped or dovetail-shaped member corresponding to the first track.

3. The apparatus of claim 1, wherein the medial rail comprises a radiolucent material, and contains therein a radiopaque element.

4. The apparatus of claim 3, wherein the radiopaque element is an elongated metal pin having a diameter that is smaller than a distance between the first side of the medial rail and a second side of the medial rail opposite the first side.

5. The apparatus of claim 4, wherein the radiopaque element is positioned between two of the plurality of holes of the medial rail.

6. The apparatus of claim 1, wherein the guide has an opening, the apparatus further comprising a bushing configured to be detachably mounted in the opening of the guide, the bushing adapted to receive a drill bit or a wire therethrough.

* * * * *